(12) United States Patent
Guerrera et al.

(10) Patent No.: US 11,090,054 B2
(45) Date of Patent: Aug. 17, 2021

(54) STAPLING DEVICE WITH RESETTABLE TILT ANVIL ASSEMBLY

(71) Applicant: Covidien LP, Mansfield, MA (US)

(72) Inventors: Joseph M. Guerrera, Watertown, CT (US); Charles R. Kollar, West Hartford, CT (US)

(73) Assignee: Covidien LP, Mansfield, MA (US)

( * ) Notice: Subject to any disclaimer, the term of this patent is extended or adjusted under 35 U.S.C. 154(b) by 424 days.

(21) Appl. No.: 16/035,113

(22) Filed: Jul. 13, 2018

(65) Prior Publication Data

US 2019/0038291 A1     Feb. 7, 2019

Related U.S. Application Data

(60) Provisional application No. 62/541,802, filed on Aug. 7, 2017.

(51) Int. Cl.
    *A61B 17/115*     (2006.01)
    *A61B 17/072*     (2006.01)
    (Continued)

(52) U.S. Cl.
    CPC .... *A61B 17/1155* (2013.01); *A61B 17/00234* (2013.01); *A61B 17/07207* (2013.01);
    (Continued)

(58) Field of Classification Search
    CPC ........ A61B 17/115; A61B 2017/07257; A61B 2017/00367
See application file for complete search history.

(56) References Cited

U.S. PATENT DOCUMENTS 3,193,165 A    7/1965   Akhalaya et al.
3,388,847 A    6/1968   Kasulin et al.
(Continued)

FOREIGN PATENT DOCUMENTS

CA       908529 A     8/1972
CA     2805365 A1    8/2013
(Continued)

OTHER PUBLICATIONS

European Search Report dated Mar. 6, 2019, issued in EP Appln. No. 18187603.

*Primary Examiner* — Andrew M Tecco
(74) *Attorney, Agent, or Firm* — Carter, DeLuca & Farrell LLP

(57) ABSTRACT

A surgical stapling device includes an anvil assembly having a center rod and an anvil head that is pivotally coupled to the center rod. The anvil head supports a cut ring assembly that is movable between a pre-fired or retracted position in which the cut ring is positioned to retain the anvil head in an operative position and an advanced position in which the cut ring assembly is positioned to allow movement of the anvil head to a tilted position. The anvil assembly also includes at least one support member that is movable from a pre-fired position extending into the anvil head to an advanced position extending from the distal end of the anvil head to allow the cut ring assembly to move from the first position to the second position. The at least one support member can be returned to the pre-fired position after the stapling device is fired and the anvil head has tilted to reset the anvil head to the operative position.

19 Claims, 8 Drawing Sheets

(51) Int. Cl.
*A61B 17/00* (2006.01)
*A61B 17/02* (2006.01)

(52) U.S. Cl.
CPC . *A61B 17/0293* (2013.01); *A61B 2017/00367* (2013.01); *A61B 2017/00473* (2013.01); *A61B 2017/07257* (2013.01); *A61B 2017/07271* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main |
| 5,588,579 A * | 12/1996 | Schnut ............... A61B 17/115 227/175.1 |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |

(56) References Cited

U.S. PATENT DOCUMENTS

| | | |
|---|---|---|
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck |
| 6,676,671 B2 | 1/2004 | Robertson et al. |
| 6,681,979 B2 | 1/2004 | Whitman |
| 6,685,079 B2 | 2/2004 | Sharma |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 * | 10/2008 | Milliman ............ A61B 17/068 227/178.1 |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |

(56) References Cited

U.S. PATENT DOCUMENTS

| | | |
|---|---|---|
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,782,173 B2 * | 10/2017 | Mozdzierz ....... A61B 17/07292 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |

(56) References Cited

U.S. PATENT DOCUMENTS

| | | |
|---|---|---|
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0092720 A1* | 4/2013 | Williams ............ A61B 17/115 227/181.1 |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0252062 A1* | 9/2014 | Mozdzierz ....... A61B 17/07292 227/175.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0000475 A1* | 1/2017 | Sgroi, Jr. ............ A61B 17/1155 |
| 2017/0020527 A1* | 1/2017 | Williams ............ A61B 17/1155 |
| 2018/0206846 A1* | 7/2018 | Guerrera ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3111858 A2 | 1/2017 |
| EP | 3120785 A1 | 1/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

STAPLING DEVICE WITH RESETTABLE TILT ANVIL ASSEMBLY

CROSS-REFERENCE TO RELATED APPLICATIONS

This application claims the benefit of and priority to U.S. Provisional Patent Application Ser. No. 62/541,802 filed Aug. 7, 2017, the entire disclosure of which is incorporated by reference herein.

BACKGROUND

1. Technical Description

The present disclosure is directed to surgical stapling devices and, more particularly, to circular stapling devices with tilt anvil assemblies that are configured for reuse.

2. Background of Related Art

Circular stapling devices for performing surgical procedures such as anastomoses, hemorrhoidectomies, and mucosectomies are well known. These devices include an anvil assembly having a center rod and an anvil head supported on the center rod. Typically, during a surgical procedure performed with a circular stapling device, the tool assembly of the stapling device is inserted into a tubular section or sections of tissue to remove diseased or damaged tissue from within the tissue section or join the tissue sections. In order to minimize trauma to the tissue section(s), the anvil head may be pivotally supported on the center rod to reduce the profile of the anvil head during insertion and/or removal of the tool assembly from within the tissue section. In some stapling devices, a component is fractured during firing of the stapling device to facilitate tilting of the anvil head.

Due to the rising costs associated with medical procedures, reusable surgical instrumentation is desirable. Thus, a circular stapling device including a reusable or resettable tilt anvil assembly is desirable.

SUMMARY

One aspect of the present disclosure is directed to a surgical stapling device including a handle assembly, an elongated body and a tool assembly. The elongated body has a proximal portion coupled to the handle assembly, a distal portion, and an anvil retainer that extends from the distal portion of the elongated body and is movable from a retracted position to an advanced position. The tool assembly is supported on the distal portion of the elongated body and includes a shell assembly and an anvil assembly. The shell assembly has an annular staple cartridge that supports a plurality staples. The anvil assembly includes a center rod assembly and an anvil head assembly. The center rod assembly includes a center rod defining a longitudinal axis and having a proximal portion and a distal portion. The proximal portion of the center rod is configured to engage the anvil retainer of the elongated body.

The anvil head assembly is pivotally secured to the distal portion of the center rod and includes a housing and a cut ring assembly. The housing defines a recess and at least one hole communicating with the recess. The housing supports a post that is disposed within the recess and an annular tissue contact surface that defines a plurality of staple deforming pockets positioned about the recess. The post defines a longitudinal axis. The cut ring assembly is movable about the post between a retracted position and an advanced position. The anvil head assembly also includes at least one support member that extends through the at least one hole in the housing. The at least one support member is movable between a retracted position in which the support member is positioned within the recess to obstruct movement of the cut ring assembly from the retracted position to the advanced position and an advanced position in which the at least one support member extends from a distal end of the at least one hole.

In another aspect of the disclosure, an anvil assembly includes a center rod assembly and an anvil head assembly. The center rod assembly includes a center rod defining a longitudinal axis, a proximal portion, and a distal portion. The anvil head assembly is pivotally secured to the distal portion of the center rod and includes a housing and a cut ring assembly. The housing defines a recess and at least one hole communicating with the recess. The housing supports a post that is disposed within the recess and an annular tissue contact surface that defines a plurality of staple deforming pockets positioned about the recess. The post defines a longitudinal axis. The cut ring assembly is movable about the post between a retracted position and an advanced position. At least one support member extends through the at least one hole in the housing and is movable between a retracted position in which the support member is positioned within the recess to obstruct movement of the cut ring assembly from the retracted position to the advanced position and an advanced position in which the at least one support member extends from a distal end of the at least one hole.

In embodiments, the anvil head assembly is pivotal from an operative position in which the longitudinal axis of the center rod is aligned with the longitudinal axis of the post to a tilted position in which the longitudinal axis of the center rod and the longitudinal axis of the post define an acute angle.

In some embodiments, the cut ring assembly is positioned to engage the center rod to retain the anvil head assembly in the operative position in the retracted position, and is positioned to permit pivotal movement of the anvil head assembly to the tilted position in the advanced position.

In certain embodiments, the at least one hole in the housing of the anvil head assembly includes a plurality of holes and the at least one support member includes a plurality of support members.

In embodiments, each of the plurality of support members is resilient and is positioned within a respective one of the plurality of openings in frictional engagement with a wall defining the respective opening.

In some embodiments, each of the plurality of support members is U-shaped and includes a crown and a pair of legs.

In certain embodiments, the cut ring assembly is supported on a backup member and the crown of each of the plurality of support members engages the backup member when the cut ring assembly is in the retracted position.

In embodiments, the backup member defines a plurality of openings and each of the plurality of support members is received within a respective one of the plurality of openings of the backup member.

In some embodiments, each of the plurality of support members includes a raised rib on at least one leg of the pair of legs. The raised rib is configured to increase a force required to move the support member through the respective opening in the housing from its retracted position to its advanced position.

In certain embodiments, the center rod assembly includes a plunger and a plunger spring, wherein the plunger spring is positioned to urge the plunger towards the anvil head assembly to urge the anvil head assembly from the operative position towards the tilted position.

BRIEF DESCRIPTION OF THE DRAWINGS

Various embodiments of the presently disclosed stapling device are described herein below with reference to the drawings, wherein.

DETAILED DESCRIPTION OF EMBODIMENTS

Figure 1:
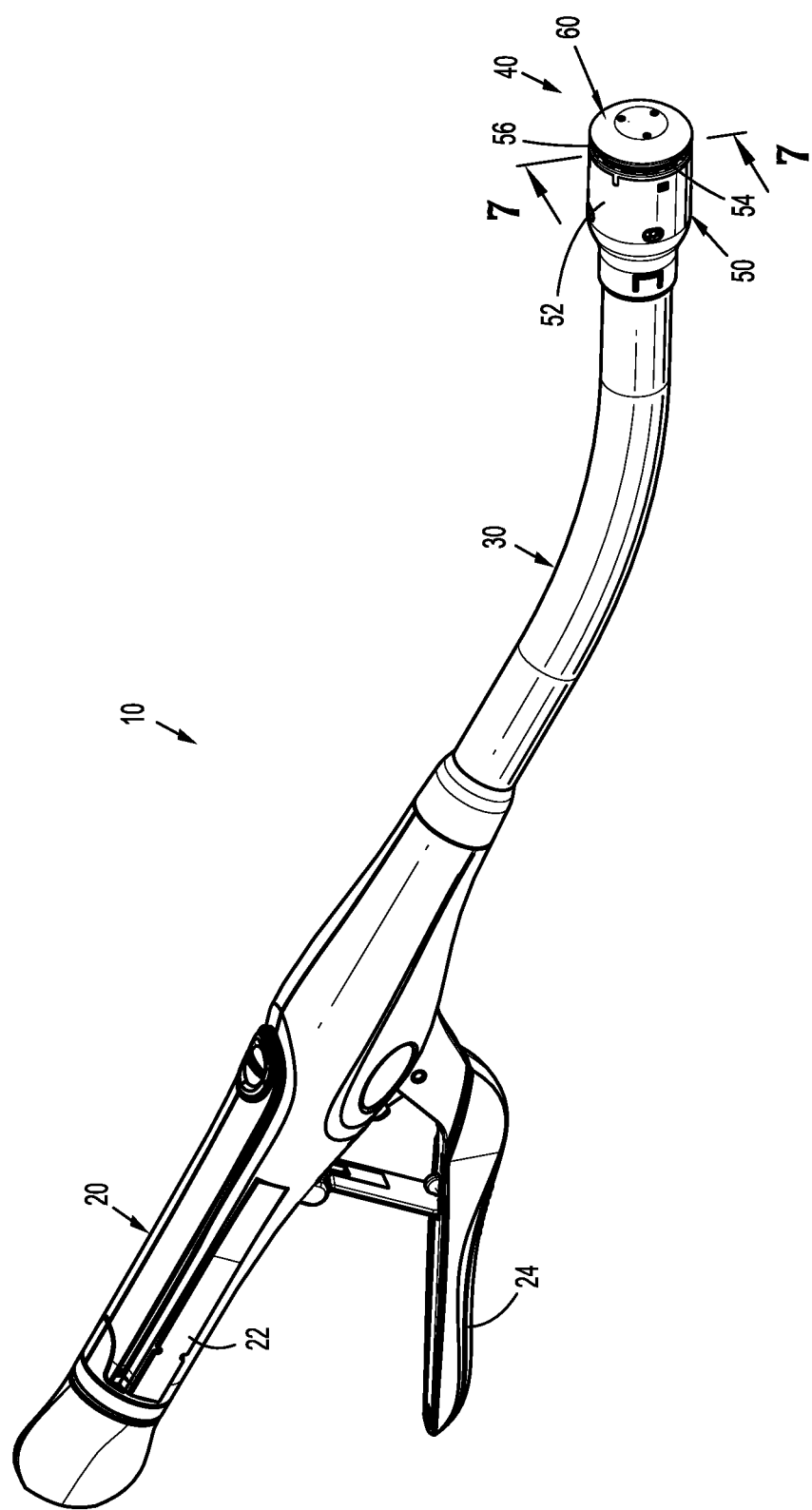
FIG. 1 is a side perspective view of an exemplary embodiment of the presently disclosed stapling device in a clamped, unfired state with an anvil head of an anvil assembly of a tool assembly of the stapling device in an operative position.

The presently disclosed stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is generally used to refer to endoscopic, laparoscopic, arthroscopic, and/or any other procedure conducted through small diameter incision or cannula. In addition, the term "clinician" is used generally to refer to medical personnel including doctors, nurses, and support personnel.

The presently disclosed surgical stapling device includes a handle or actuator assembly, an elongate body or adaptor, and a tool assembly coupled to a distal portion of the adaptor. The tool assembly includes a tilt anvil assembly and a shell assembly. The tilt anvil assembly includes a center rod that is releasably coupled to the adaptor and an anvil head that is pivotally coupled to the center rod. The anvil head supports a cut ring assembly that is movable between a pre-fired or retracted position in which the cut ring assembly retains the anvil head in an untilted or operative position and an advanced position in which the cut ring assembly is positioned to allow movement of the anvil head to a tilted position.

The anvil assembly also includes at least one support member that is movable from a pre-fired position extending into the anvil head to an advanced position extending from the anvil head to allow the cut ring assembly to move from the first position to the second position. In embodiments, the at least one support member includes a plurality of support members, e.g., 2-8, that extend into the anvil head of the anvil assembly to retain the cut ring assembly in the retracted position to retain the anvil head in the operative position. The plurality of support members can be returned to the pre-fired position after the stapling device is fired to reset the anvil head to the operative position as described in further detail below.

Figure 2:
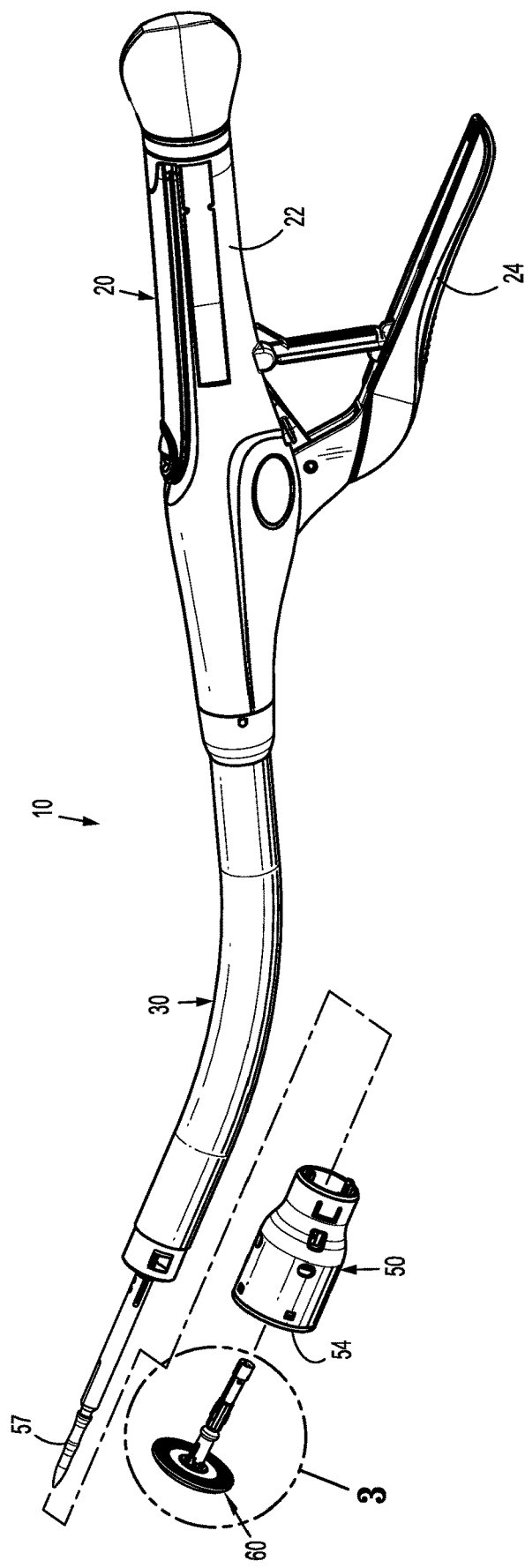
FIG. 2 is a side perspective view of the stapling device shown in FIG. 1 with the tool assembly separated from an elongate body portion of the stapling device.

Referring to FIGS. 1 and 2, the presently disclosed surgical stapling device is shown generally as stapling device 10 and includes a handle or actuator assembly 20, an elongate body 30, and a tool assembly 40. The handle assembly 20 as illustrated is an manually powered assembly and includes a grip 22 and a firing trigger 24 that can be moved through a first actuation stroke to move the stapling device 10 to a clamped state and subsequent actuation strokes to fire the stapling device 10. Examples of manually powered handle assemblies are described in U.S. Pat. Nos. 8,789,737, 8,424,535 ('535 patent) and U.S. Pat. No. 8,360,295 which are incorporated herein in their entirety by reference.

It is also envisioned that the stapling device 10 could be electrically powered. In embodiments, the elongate body 30 can be releasably coupled to a distal portion of the handle assembly 20 and may include a plurality of drive mechanisms (not shown) that translate power from the handle assembly 20 to the tool assembly 40 in response to actuation of the handle assembly 20 to effect operation, i.e., approximation and firing, of the tool assembly 40. U.S. Pat. Nos. 9,247,940, 9,055,943, and 8,806,973, and U.S. Publication No. 2015/0014392 disclose exemplary embodiments of powered handle assemblies and adaptor assemblies and are incorporated herein by reference in their entirety.

The tool assembly 40 includes a shell assembly 50 and an anvil assembly 60. The shell assembly 50 includes a housing 52 that supports a staple cartridge 54 having an annular array of staple pockets 56. Each of the staple pockets 56 houses a staple (not shown). The shell assembly 50 also includes components that facilitate firing of the staples from the staple cartridge 54 and an annular knife 58 (FIG. 7) that is movable from a retracted position recessed within the housing 52 (FIG. 7) to an advanced position extending into the anvil assembly 60 (FIG. 8). An anvil retainer 57 (FIG. 2) extends distally from the shell assembly 50 and is configured to releasably engage the anvil assembly 60. The '535 patent describes the components of a shell assembly suitable for use with the presently disclosed stapling device 10. As illustrated in FIG. 2, the tool assembly 40, including the shell assembly 50 and the anvil assembly 60, can be removable from the elongate body 30 of the stapling device 10.

Referring to FIGS. 3-6, the anvil assembly 60 includes a center rod assembly 62 and an anvil head assembly 64 that is pivotally supported on a distal portion of the center rod assembly 62. The anvil head assembly 64 includes a housing 70 including a post 72 and an anvil tissue contact surface 74, a backup member 76, a cut ring assembly 78, a cam latch member 80, and a plurality of support members 82. In embodiments, the housing 70, the post 72, and the anvil tissue contact surface 74 are monolithically formed. Alternately, any one or all of the housing 70, post 72, and anvil tissue contact surface 74 can be formed separately and secured together using any known fastening technique including welding, crimping or the like. The housing 70 of the anvil head assembly 64 defines a recess 86 (FIG. 4) positioned between the post 72 and the tissue contact surface 74 with the post 72 centrally located within the recess 86. The tissue contact surface 74 of the housing 70 faces a tissue contact surface of the staple cartridge 54 (FIG. 1) and includes a plurality of staple deforming pockets 92 for receiving and deforming staples ejected from the staple cartridge 54.

Figure 3:
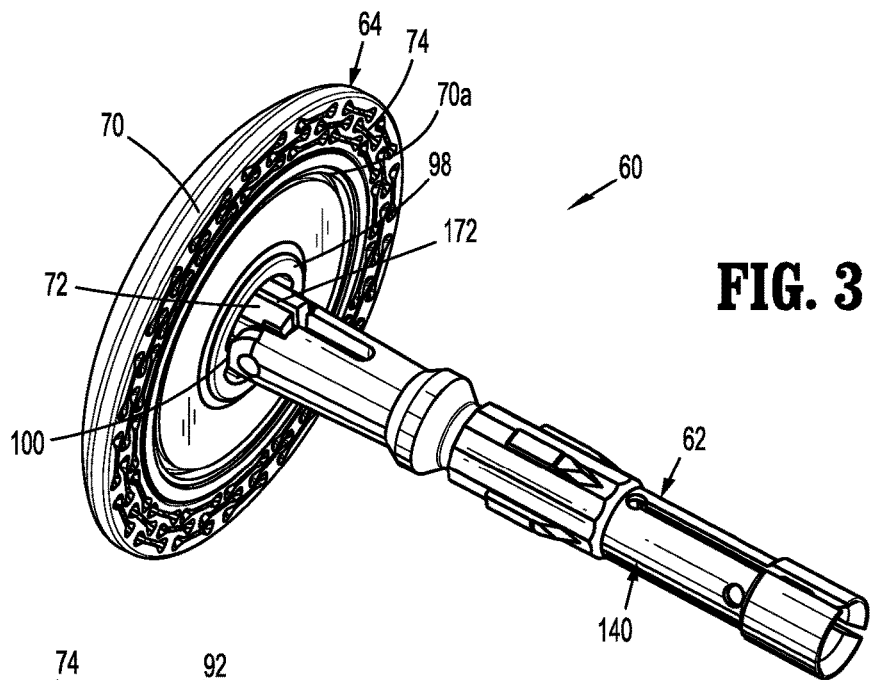
FIG. 3 is an enlarged view of the indicated area of detail shown in FIG. 2.

The housing 70 of the anvil head assembly 64 also defines one or more reset holes 75 (FIG. 4) that extend through a distal face of the housing 70 and communicate with the recess 86 (FIG. 3). Although three reset holes 75 are shown in the illustrated embodiment, the housing 70 may define one or more reset holes, e.g., 1-6. The reset holes 75 communicate with the recess 86 (FIG. 4) at a position axially aligned with the backup member 76 and are configured and dimensioned to receive a respective one of the plurality of support members 82. The reset holes 75 may also function as vent holes that allow fluid, e.g., blood, tissue, etc., to escape from within the tool assembly 40 during clamping and firing of the stapling device 10.

Figure 4:
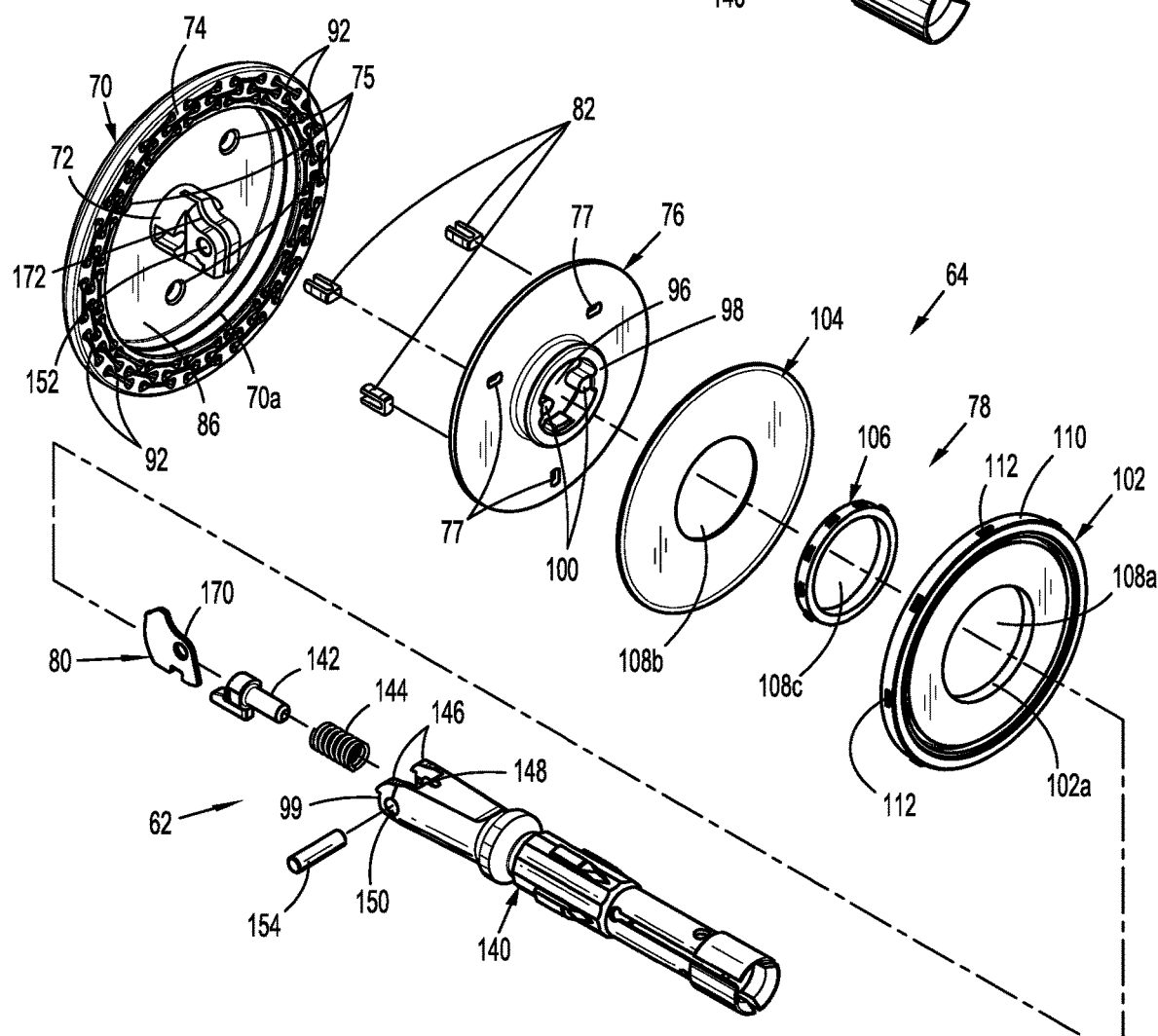
FIG. 4 is an exploded, side perspective view of the anvil assembly shown in FIG. 2.
Figure 5:
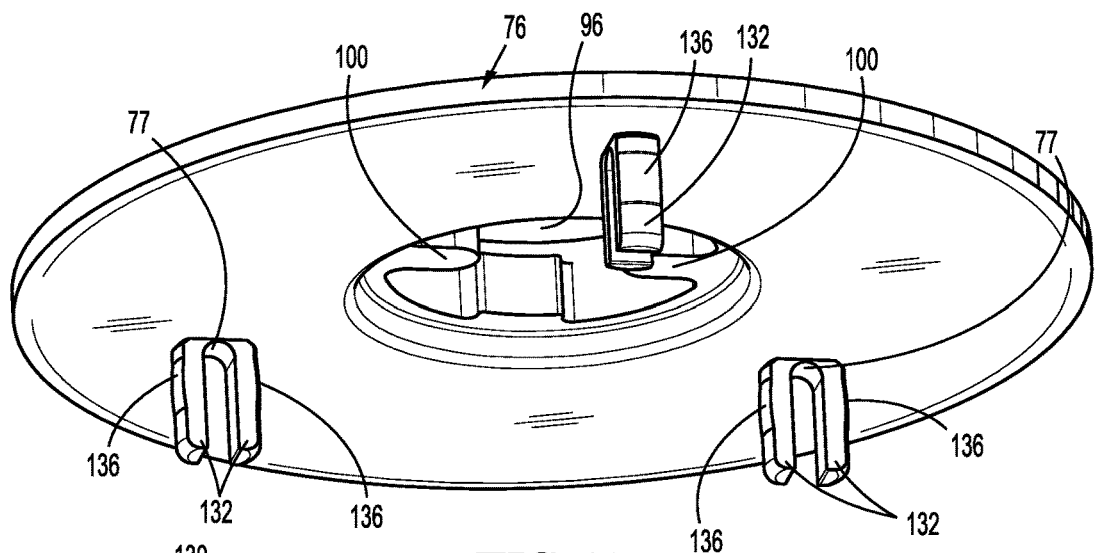
FIG. 5 is a perspective from the distal end of a backup ring of the anvil assembly shown in FIG. 4.

With particular reference to FIGS. 3-5 the backup member 76 defines a central opening 96 and a plurality of openings 77. The central opening 96 is dimensioned to receive the post 72 (FIG. 4) of the housing 70 of the anvil head assembly 64 and the plurality of openings 77 are dimensioned to receive the plurality of support members 82 as described in further detail below. The central opening 96 is dimensioned to facilitate movement of the backup member 76 about the post 72 from a pre-fired, retracted position (FIG. 7) to a post-fired, advanced position (FIG. 8) within the recess 86 (FIG. 4) of the housing 70. The backup member 76 includes a raised flange 98 that is positioned about the opening 96. Although the raised flange 98 is illustrated as having a circular shape, other configurations are envisioned, e.g., square, rectangular, triangular, etc.

The backup member 76 includes a pair of inwardly extending fingers 100 that are movable into and out of engagement with a distal flat 99 (FIG. 4) of the center rod assembly 62 of the anvil assembly 60 to allow the anvil head assembly 64 to pivot in relation to the center rod assembly 62 between operative and tilted position as discussed in detail below. In embodiments, the backup member 76 is formed from a hard material such as metal although the use of other suitable materials of construction is envisioned.

U.S. Pat. No. 8,540,132 (the '132 patent) which is incorporated herein in its entirety by reference discloses a tilt anvil assembly that includes a backup member and cut ring assembly that are movably positioned about a post of an anvil head of an anvil assembly.

In embodiments, the cut ring assembly 78 (FIG. 4) includes an annular body 102 formed of a first material, an annular base member 104 formed of a second material, and an annular inner sleeve 106. The body 102, base member 104, and sleeve 106 of the cut ring assembly 78 define openings 108a-c, respectively, that are configured to receive the flange 98 of the backup member 76. The sleeve 106 is secured to an inner surface 102a of the body 102 and is positioned about the flange 98 of the backup member 76 to secure the cut ring assembly 78 to the backup member 76. Movement of the backup member 76 between retracted and advanced positions about the post 72 of the anvil head 70 causes corresponding movement of the cut ring assembly 78 about the post 72 of the anvil head 70.

In some embodiments, the sleeve 106 is formed from a hard plastic material that is over molded onto the inner surface 102a of the body 102 of the cut ring assembly 78. In certain embodiments, the sleeve 106, after being overmolded onto the body 102 of the cut ring assembly 78, is press-fit onto the flange 98 of the backup member 76 to secure the sleeve 106 and the body 102 onto the backup member 76. The body 102 may be secured to the base member 104 with an adhesive or the like such that the base member 104 is sandwiched between the body 102 and the backup member 76. Alternately, the base member 104 can be pressed between the body 102 and the backup member 75 without the use of an adhesive.

In embodiments, the body 102 of the cut ring assembly 78 is formed from a first material having a first durometer, e.g., polypropylene, and the base member 104 is formed of a second material having a second lower durometer e.g., polyester. The above described construction of the cut ring assembly 78 allows the knife 58 (FIG. 8) to initially pierce through the soft durometer material of the body 102, and then pierce the second lower durometer material of the base member 104, and finally to bottom out against the harder material of the backup plate 76.

It is envisioned that a variety of cut ring assemblies can be included in the presently disclosed anvil head assembly 64. For example, the cut ring assembly 78 need not include a sleeve and/or a base member 104 and may be formed of only a single layer.

Figure 7:
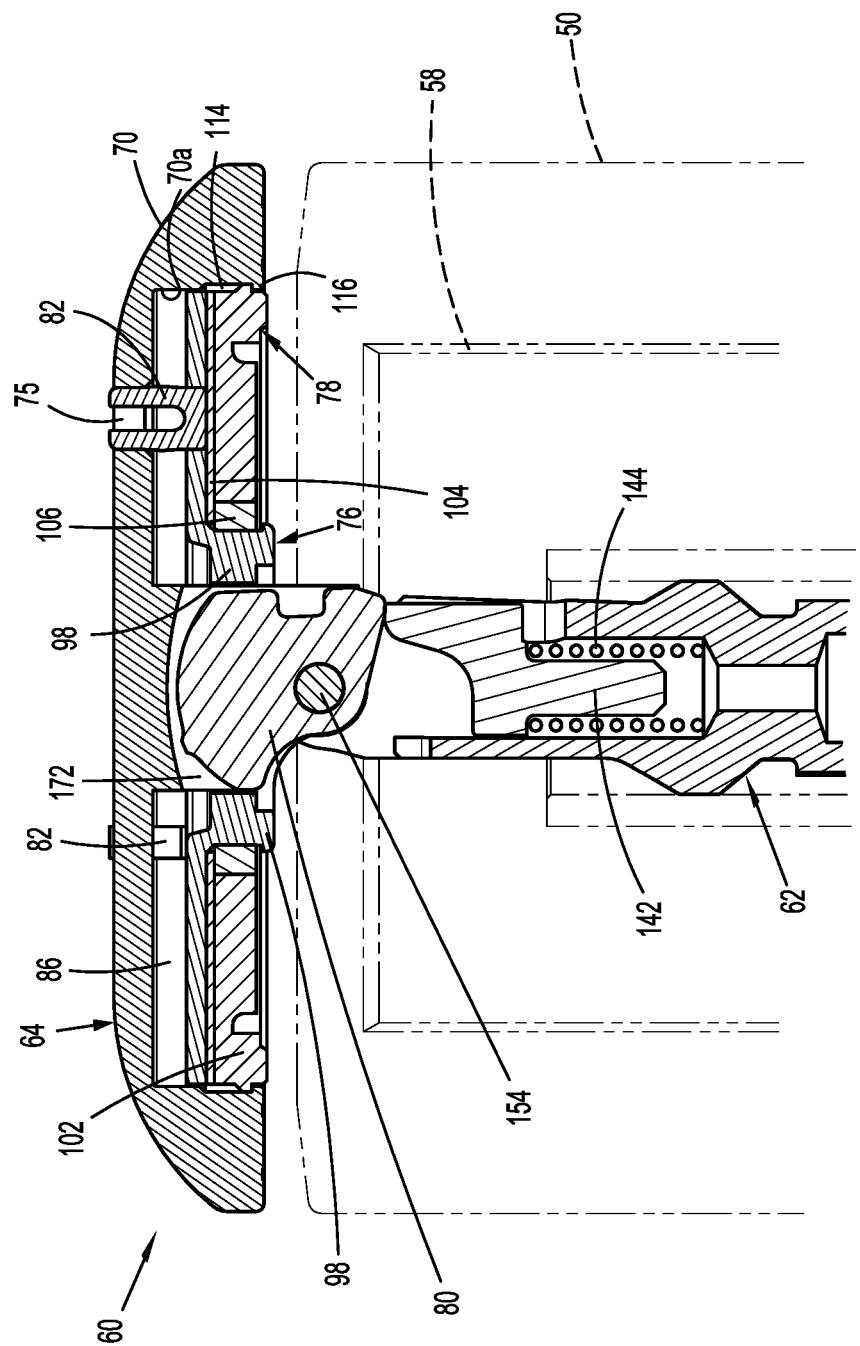
FIG. 7 is a cross-sectional view taken along section line 7-7 of FIG. 1 with the stapling device in the clamped, unfired state and the anvil head of the anvil assembly in the operative position.
Figure 8:
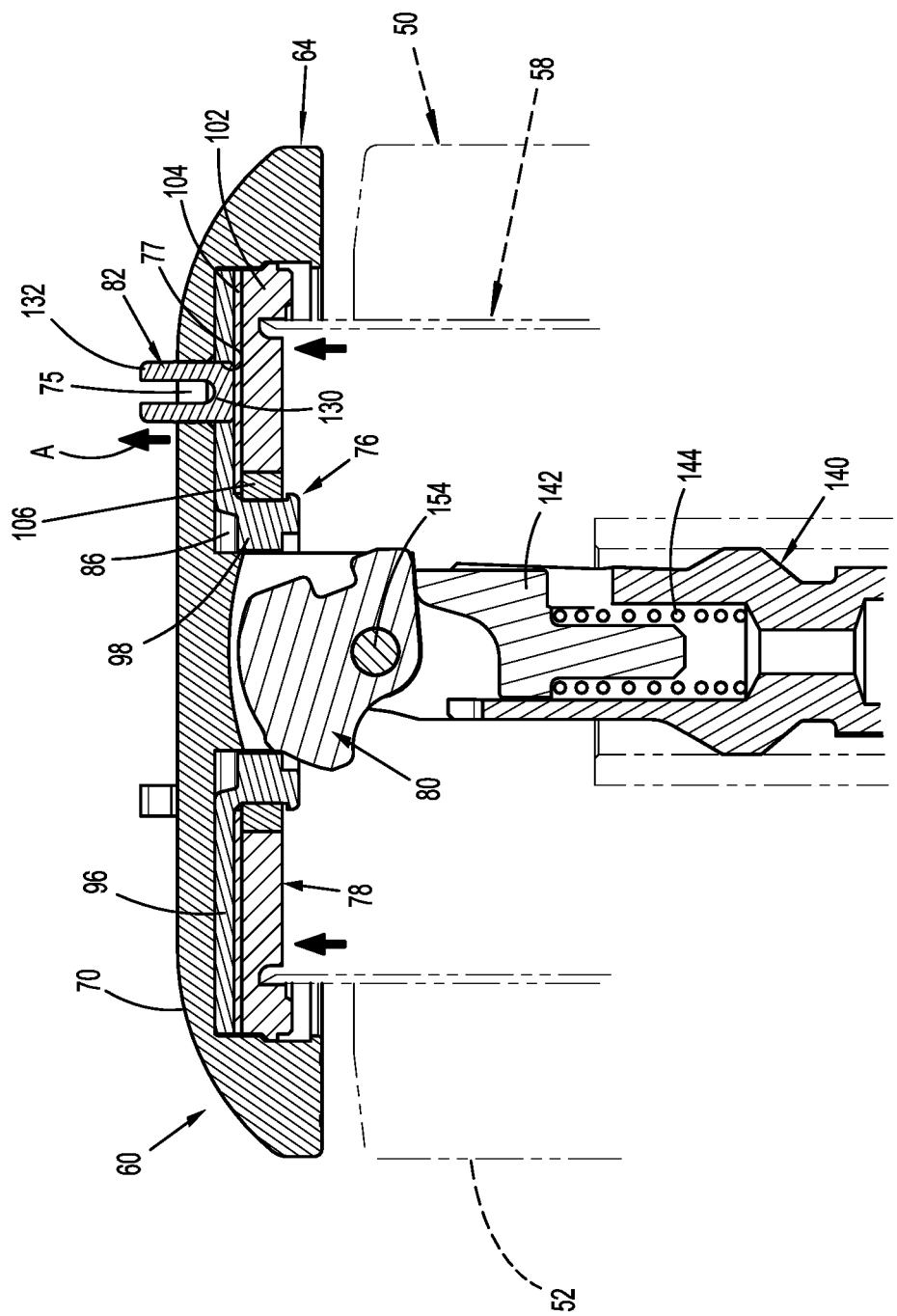
FIG. 8 is a cross-sectional view taken along section line 7-7 of FIG. 1 with the stapling device in a clamped, fired state and the anvil head in the operative position.

Referring to FIGS. 4, 7 and 8, the body 102 of the cut ring assembly 78 includes an outer wall 110 (FIG. 3) having a series of projections 112 and the housing 70 of the anvil assembly 60 includes an inner wall 70a (FIG. 7) defining an annular groove 114. In embodiments, the projections 112 of the body 102 of the anvil head assembly 64 are slidably received within the annular groove 114 to guide movement of the cut-ring assembly 78 and backup member 76 between their advanced and retracted positions within the recess 86 (FIG. 4) of the housing 70. An annular stop member 116 (FIG. 7) is formed on the housing 70 at a proximal end of the annular groove 114. The annular stop member 116 and the projections 112 of the body 102 of cut ring assembly 78 are configured to engage each other to retain the cut ring assembly 78 and backup plate 76 within the recess 86 of the housing 70 of the anvil head assembly 60.

Figure 5A:
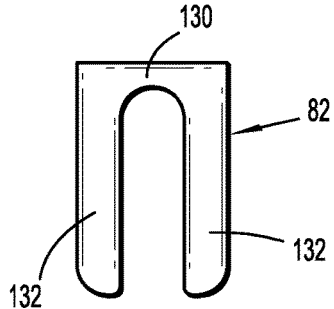
FIG. 5A is a perspective view of a support member of the anvil assembly shown on FIG. 4.

Referring to FIGS. 5, 5A and 7, each of the plurality of support members 82 is supported within a respective one of the reset holes 75. In embodiments, each of the plurality of support members 82 includes a substantially U-shaped body (FIG. 5) having a crown 130 and a pair of spaced, resilient legs 132. The legs 132 are flexible and extend through the reset holes 75 (FIG. 7) such that the legs 132 are biased inwardly and frictionally engaged by walls of the housing 70 defining the reset holes 75. The crown 130 of each of the support members 82 is received in a respective one of the openings 77 of the backup member 76. Due to the frictional engagement of the legs 132 of the support members 82 with the housing 70 of the anvil head assembly 64, the support members 82 resist axial movement until a predetermined force is applied to the support members 82. The outer surface of each of the legs 132 may include a raised rib 136 (FIG. 5) that is positioned to engage the walls of the housing 70 defining the reset holes 75 to increase the resistance to axial movement of the support member 82. It is envisioned that the support members 82 may assume a variety of different configurations provided that the support members 82 resist axial movement until a predetermined axial force is applied to the support members 82 by the backup member 76.

Figure 6:
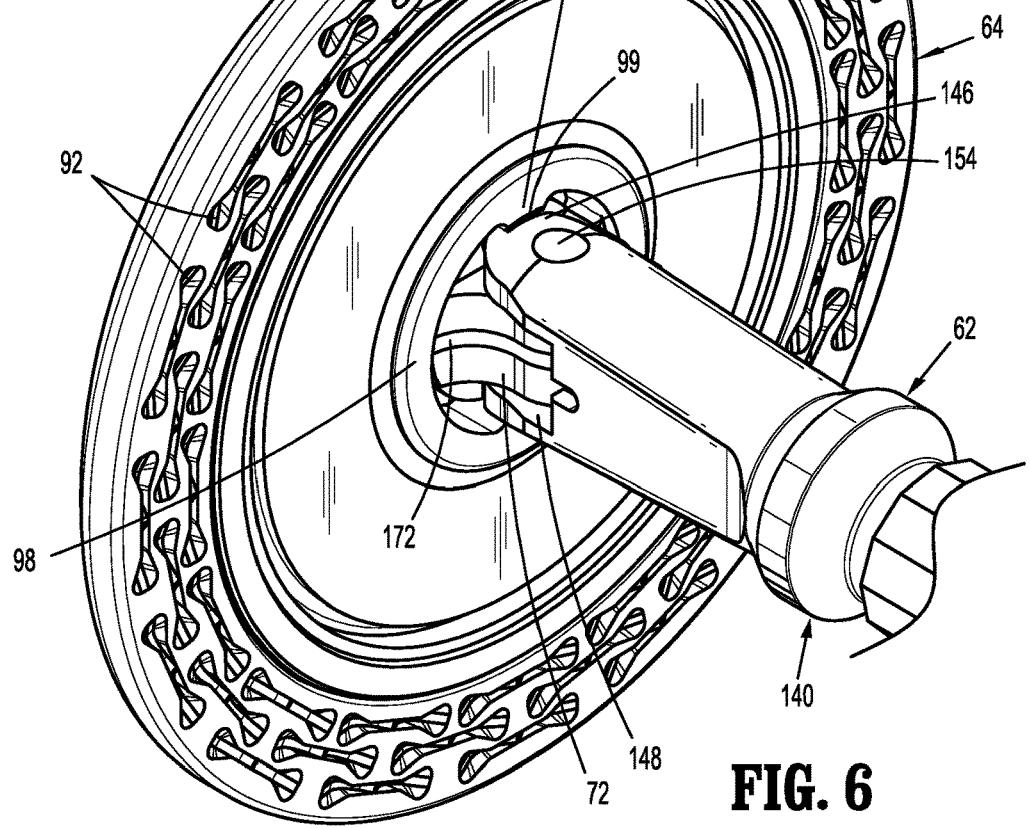
FIG. 6 is a perspective view from the proximal end of a distal portion of the anvil assembly shown in FIG. 2.
Figure 10:
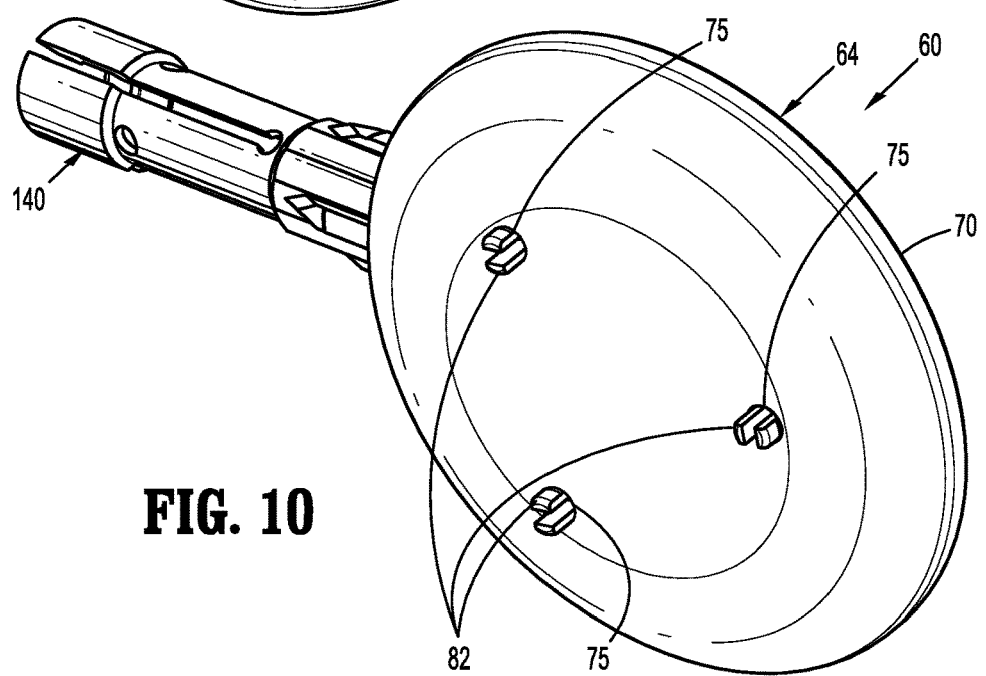
FIG. 10 is a side perspective view of the anvil assembly shown in FIG. 3 after the stapling device is fired with the anvil head in the tilted position.

With reference again to FIGS. 3-7, the center rod assembly 62 includes a center rod 140, a plunger 142, and a plunger spring 144 (FIG. 4). A first end of center rod 140 includes spaced arms 146 that define a cavity 148 (FIG. 4) dimensioned to receive the post 72 of the anvil head assembly 64. Each of the arms 146 of the center rod 140 has distally facing flat 99 and a transverse through bore 150. The transverse through bores 150 define an axis that intersects a central longitudinal axis of center rod 140. Alternately, the through bore 150 axis can be offset from the longitudinal axis of center rod 62. The post 72 of anvil head assembly 64 is dimensioned to be positioned within cavity 148 defined between the spaced arms 146 of the center rod 62 and also includes a transverse through bore 152. A pivot member 154 extends through the through bores 150 of the arms 146 and the through bore 152 of the post 72 to pivotally secure the post 72 to the center rod 140 such that the anvil head assembly 64 is pivotally mounted to the center rod assembly 62 between an operative position (FIG. 3) and a tilted position (FIG. 10). In the operative position, the longitudinal axes of the center rod 140 and the post 72 are aligned. In the tilted position, the longitudinal axes of the center rod 140 and the post 72 define an acute angle. The distally facing flats 99 formed on the distal end of the center rod 140 are dimensioned to abut the inwardly extending fingers 100 of the backup member 76 when the backup member 76 is in the retracted position within the recess 86 of the housing 70 to releasably retain the anvil head assembly 64 in the operative position as discussed in further detail below (FIG. 6).

The cam latch member 80 (FIG. 4) is received in a cutout 172 (FIG. 8) defined within the post 72 of the anvil head assembly 64. The cam latch member 80 defines a through bore 170 (FIG. 4) that receives the pivot member 154 such that the cam latch member 80 is pivotally supported about the pivot member 154 within the cutout 172. The plunger 142 is urged by the plunger spring 144 (FIG. 4) into engagement with the cam latch member 80 and a proximal end of the post 72 of the anvil head assembly 64 to urge the anvil head assembly 64 about the pivot member 154 towards the tilted position (FIG. 10). The cam latch member 80 is configured to engage the inner surface of the backup member 76 (FIG. 7) to prevent movement of the backup member 76 and the cut ring assembly 78 from the advanced position within the recess 86 (FIG. 7) back to the retracted position after the stapling device 10 is fired.

For a more detailed description of anvil assembly 60 including operation of the cam latch member 80, the plunger 142, and the plunger spring 144, see the '132 patent.

Referring to FIG. 7, prior to firing of the stapling device 10 (FIG. 1), the backup member 76 and the cut ring assembly 78 are in their retracted positions with the cut ring assembly 78 supported about the flange 98 of the backup member 76. The support members 82 extend through the reset holes 75 into the recess 86 of the housing 70 of the anvil head assembly 64 and into the openings 77 of the backup member 76. In this position, the support members 82 obstruct movement of the backup member 76 and cut ring assembly 78 from the retracted position (FIG. 7) within the recess 86 of the housing 70 towards the advanced position (FIG. 8).

With the backup member 76 in its retracted position, the inwardly extending fingers 100 (FIG. 6) of the backup member 76 are supported on the distally facing flats 99 (FIG. 6) of the center rod 140 such that the anvil head assembly 64 is retained in the operative position. As discussed above, the plunger 142 of the center rod assembly 62 is positioned to urge the cam latch member 80 and the anvil head assembly 62 about the pivot member 154 towards the tilted position (FIG. 10).

Figure 9:
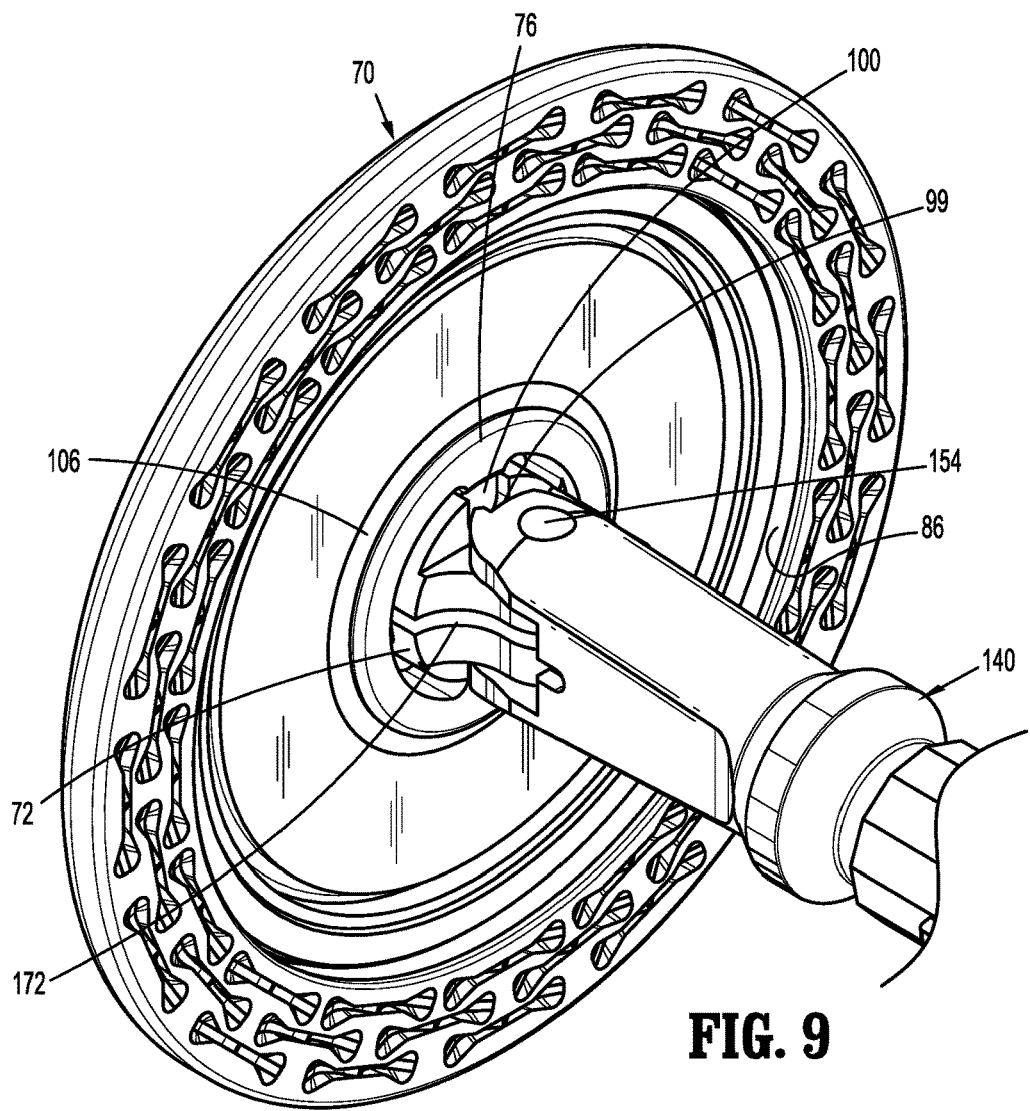
FIG. 9 is a perspective view of the distal portion of the anvil assembly shown in FIG. 2 from the proximal end after the stapling device is fired but prior to movement of the anvil head of the anvil assembly to the tilted position.

Referring to FIGS. 8-10, when the stapling device 10 (FIG. 1) is approximated and subsequently fired, the annular knife 58 (FIG. 8) of the shell assembly 50 is advanced from a retracted position (FIG. 7) recessed within the housing 52 of the shell assembly 50 to an advanced position extending into the cut ring assembly 78 of the anvil head assembly 64. As the annular knife 58 engages the cut ring assembly 78, the cut ring assembly 78 and the backup member 76 are advanced from their retracted positions to their advanced positions within the recess 86 of the housing 70 of the anvil head assembly 64. As discussed above, the crown of the support members 82 are received within openings 77 (FIG. 8) of the backup member 76. Thus, when the backup member 76 moves towards its advanced position, the support members 82 are also advanced distally through the reset holes 75 in the direction indicated by arrow "A" in FIG. 8 from a position extending proximally into the recess 86 of the housing 70 of the anvil head assembly 64 to a position extending distally from the reset holes 75. As the resilient legs 132 of the support members 82 are advanced through the reset openings 75, the resilient legs 132 are deformed inwardly to facilitate passage through the reset openings 75.

As discussed above, when the backup member 76 moves to its advanced position, the inwardly extending fingers 100 (FIG. 9) are moved to a position spaced from the distally facing flats 99 (FIG. 9) on the distal end of the center rod 140. When the fingers 100 move to a position spaced from the distally facing flats 99 of the center rod 140 and the stapling device 10 is moved to the spaced position in relation to the shell assembly 50, the plunger spring 144 (FIG. 4) urges the plunger 142 into the cam latch member 80 and post 72 to urge the anvil head assembly 64 towards the tilted position. When the anvil assembly 60 is retracted in relation to the shell assembly 50, the anvil head assembly 64 will pivot to the tilted position (FIG. 10).

Figure 11:
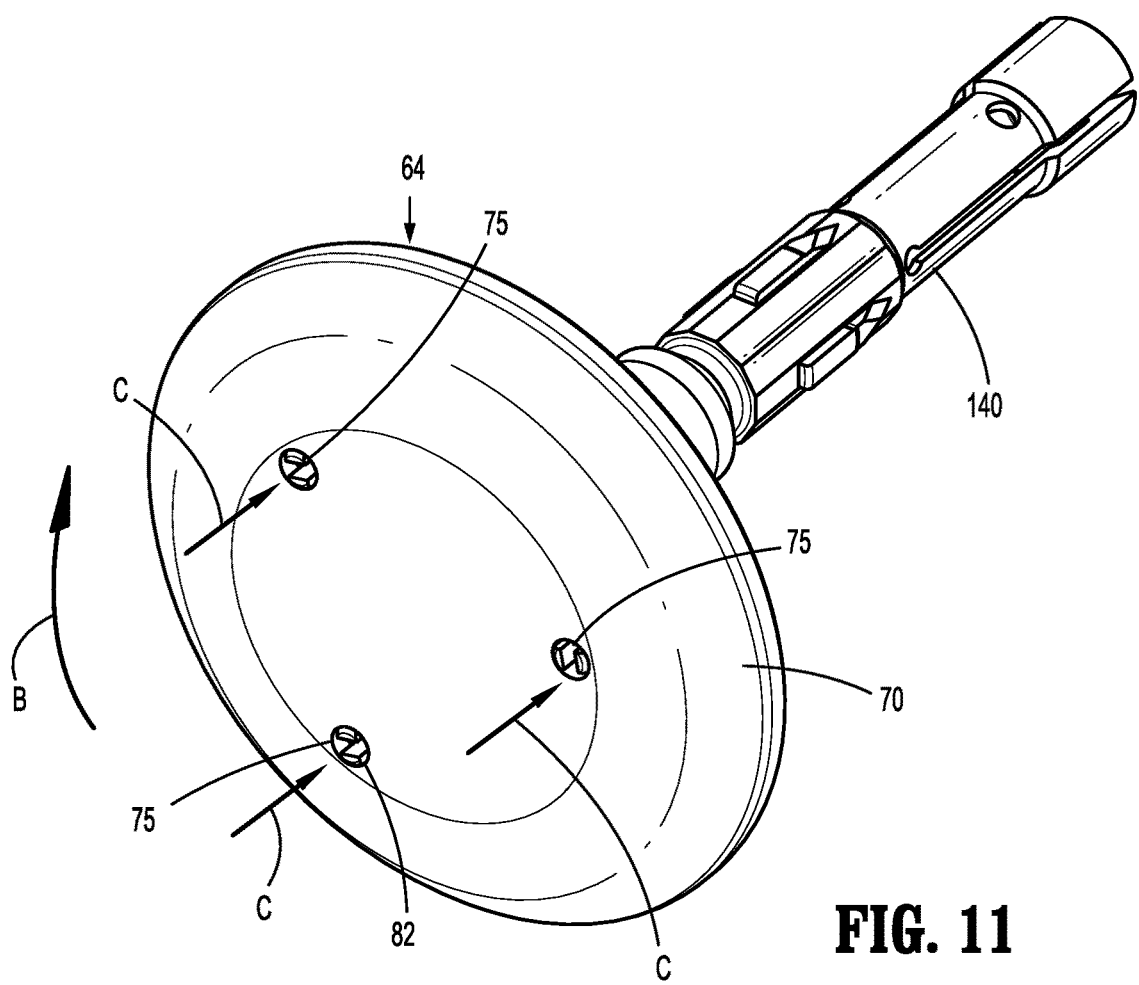
FIG. 11 is side perspective view of the anvil head of the anvil assembly as the anvil head is reset to the non-tilted position.
Figure 12:
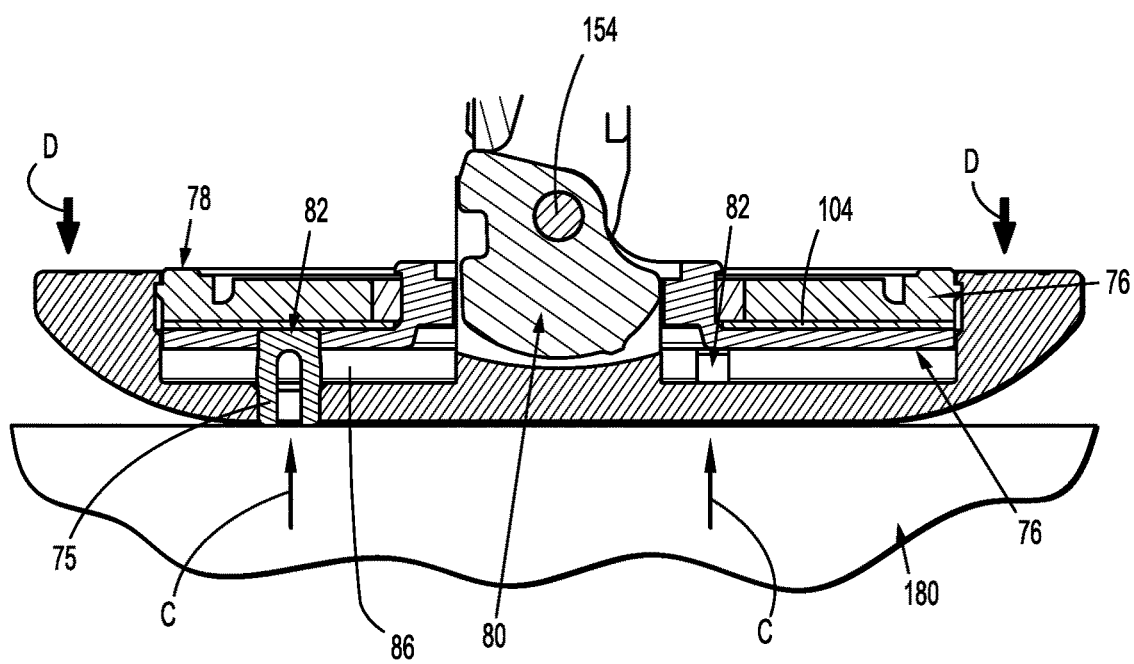
FIG. 12 is a cross-sectional view taken through the anvil head of the anvil assembly as the anvil head is reset to the non-tilted position.

Referring to FIGS. 11 and 12, after the stapling device 10 (FIG. 1) has been fired, the anvil head assembly 64 has moved to the tilted position (FIG. 10), and the tool assembly 40 has been withdrawn from a patient's body, the anvil head assembly 64 can be manually reset to the operative position (FIG. 2). More specifically, the anvil head assembly 64 can be manually reset to the operative position by manually returning the anvil head assembly 64 against the bias of spring 144 (FIG. 4) in the direction indicted by arrow "B" in FIG. 11 to the operative position. After the anvil head assembly 64 is returned to the operative position, the support members 82 can be pressed proximally back through the reset openings 75 of the housing 70 of the anvil head assembly 64 in the direction indicated by arrows "C" to return the backup member 76 and the cut ring assembly 78 to their retracted positions. This can be accomplished by pressing the distal face of the housing 70 of the anvil head assembly 64 downwardly in the direction indicated by arrows "D" against a support surface 180 (FIG. 12) to urge the support members 82 in the direction indicated by arrows "C" proximally through the reset openings 75 in the housing 70.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
a handle assembly;
an elongated body having a proximal portion coupled to the handle assembly, a distal portion, and an anvil retainer, the anvil retainer extending from the distal portion of the elongated body and being movable from a retracted position to an advanced position; and
a tool assembly supported on the distal portion of the elongated body, the tool assembly including a shell assembly and an anvil assembly, the shell assembly having an annular staple cartridge, the anvil assembly including:
a center rod assembly including a center rod defining a longitudinal axis and having a proximal portion and a distal portion, the proximal portion of the center rod being configured to engage the anvil retainer of the elongated body; and
an anvil head assembly pivotally secured to the distal portion of the center rod, the anvil head assembly including a housing and a cut ring assembly, the housing defining a recess and at least one hole communicating with the recess, the housing supporting a post disposed within the recess and an annular tissue contact surface defining a plurality of staple deforming pockets positioned about the recess, the post defining a longitudinal axis, the cut ring assembly being movable about the post between a retracted position and an advanced position, and at least one support member extending through the at least one hole in the housing, the at least one support member being movable between a retracted position in which the support member is positioned within the recess to obstruct movement of the cut ring assembly from the retracted position to the advanced position and an advanced position in which the at least one support member extends from a distalmost end of the housing through the at least one hole.

2. The stapling device of claim 1, wherein the anvil head assembly is pivotal from an operative position in which the longitudinal axis of the center rod is aligned with the longitudinal axis of the post to a tilted position in which the longitudinal axis of the center rod and the longitudinal axis of the post define an acute angle, wherein in its retracted position, the cut ring assembly is positioned to engage the center rod to retain the anvil head assembly in the operative position and in its advanced position, the cut ring assembly is positioned to permit pivotal movement of the anvil head assembly to the tilted position.

3. The stapling device of claim 1, wherein the at least one hole in the housing of the anvil head assembly includes a plurality of holes and the at least one support member includes a plurality of support members.

4. The stapling device of claim 3, wherein each of the plurality of support members is resilient and is positioned within a respective one of the plurality of openings in frictional engagement with a wall defining the respective opening.

5. The stapling device of claim 4, wherein each of the plurality of support members is U-shaped and includes a crown and a pair of legs.

6. The stapling device of claim 5, wherein the cut ring assembly is supported on a backup member, and the crown of each of the plurality of support members engaging the backup member when the cut ring assembly is in the retracted position.

7. The stapling device of claim 6, wherein the backup member defines a plurality of openings and each of the plurality of support members is received within a respective one of the plurality of openings of the backup member.

8. The stapling device of claim 7, wherein each of the plurality of support members includes a raised rib on at least one leg of the pair of legs, the raised rib being configured to increase a force required to move the support member through the respective opening in the housing from its retracted position to its distal position.

9. The surgical stapling device of claim 1, wherein the center rod assembly includes a plunger and a plunger spring, the plunger spring being positioned to urge the plunger towards the anvil head assembly to urge the anvil head assembly from the operative position towards the tilted position.

10. An anvil assembly comprising:
a center rod assembly including a center rod defining a longitudinal axis and having a proximal portion and a distal portion, the proximal portion of the center rod being configured to engage an anvil retainer of an elongated body; and
an anvil head assembly pivotally secured to the distal portion of the center rod, the anvil head assembly including a housing and a cut ring assembly, the housing defining a recess and at least one hole communicating with the recess, the housing supporting a post disposed within the recess and an annular tissue contact surface defining a plurality of staple deforming pockets positioned about the recess, the post defining a longitudinal axis, the cut ring assembly being movable about the post between a retracted position and an advanced position, and at least one support member extending through the at least one hole in the housing, the at least one support member being movable between a retracted position in which the support member is positioned within the recess to obstruct movement of the cut ring assembly from the retracted position to the advanced position and an advanced position in which the at least one support member extends from a distalmost end of the housing through the at least one hole.

11. The anvil assembly of claim 10, wherein the anvil head assembly is pivotal from an operative position in which the longitudinal axis of the center rod is aligned with the longitudinal axis of the post to a tilted position in which the longitudinal axis of the center rod and the longitudinal axis of the post define an acute angle, wherein in its retracted position, the cut ring assembly is positioned to engage the center rod to retain the anvil head assembly in the operative position and in its advanced position, the cut ring assembly is positioned to permit pivotal movement of the anvil head assembly to the tilted position.

12. The anvil assembly of claim 11, wherein the at least one hole in the housing of the anvil head assembly includes a plurality of holes and the at least one support member includes a plurality of support members.

13. The anvil assembly of claim 12, wherein each of the plurality of support members is resilient and is positioned within a respective one of the plurality of openings in frictional engagement with a wall defining the respective opening.

14. The anvil assembly of claim 13, wherein each of the plurality of support members is U-shaped and includes a crown and a pair of legs.

15. The anvil assembly of claim 14, wherein the cutting ring assembly is supported on a backup member, and the crown of each of the plurality of support members engaging the backup member when the cut ring assembly is in the retracted position.

16. The anvil assembly of claim 15, wherein the backup member defines a plurality of openings and each of the plurality of support members is received within a respective one of the plurality of openings of the backup member.

17. The anvil assembly of claim 16, wherein each of the plurality of support members includes a raised rib on at least one leg of the pair of legs, the raised rib being configured to increase a force required to move the support member through the respective opening in the housing from its retracted position to its distal position.

18. The anvil assembly device of claim 10, wherein the center rod assembly includes a plunger and a plunger spring, the plunger spring being positioned to urge the plunger towards the anvil head assembly to urge the anvil head assembly from the operative position towards the tilted position.

19. A surgical stapling device comprising:

a handle assembly;

an elongated body having a proximal portion coupled to the handle assembly, a distal portion, and an anvil retainer, the anvil retainer extending from the distal portion of the elongated body and being movable from a retracted position to an advanced position; and a tool assembly supported on the distal portion of the elongated body, the tool assembly including a shell assembly and an anvil assembly, the shell assembly having an annular staple cartridge, the anvil assembly including:

a center rod assembly including a center rod having a proximal portion and a distal portion, the proximal portion of the center rod being configured to engage the anvil retainer of the elongated body; and an anvil head assembly pivotally secured to the distal portion of the center rod, the anvil head assembly including a housing and a cut ring assembly, the housing defining a recess and at least one hole communicating with the recess, the housing supporting a post disposed within the recess and an annular tissue contact surface defining a plurality of staple deforming pockets positioned about the recess, the cut ring assembly being movable about the post between a retracted position and an advanced position, and at least one support member extending through the at least one hole in the housing, the at least one support member being configured to move from a retracted position in which the support member is positioned within the recess to obstruct movement of the cut ring assembly from the retracted position of the cut ring assembly to the advanced position of the cut ring assembly, to an advanced position in which the at least one support member extends from a distal end of the at least one hole, and back to the retracted position by pushing on the at least one support member.

* * * * *